United States Patent
Shapira et al.

(10) Patent No.: US 8,187,197 B2
(45) Date of Patent: May 29, 2012

(54) CEREBRAL PERFUSION MONITOR

(75) Inventors: Aharon Shapira, Jerusalem (IL); Alon Rappaport, Tel-Aviv (IL); Shlomi Ben-Ari, Binyamina (IL); Yosef Reichman, Kfar-Saba (IL); Ofer Barnea, Herzlia (IL)

(73) Assignee: Orsan Medical Technologies Ltd., Netania (IL)

( * ) Notice: Subject to any disclaimer, the term of this patent is extended or adjusted under 35 U.S.C. 154(b) by 1170 days.

(21) Appl. No.: 11/572,141

(22) PCT Filed: Jun. 15, 2005

(86) PCT No.: PCT/IL2005/000632
§ 371 (c)(1),
(2), (4) Date: Jul. 3, 2007

(87) PCT Pub. No.: WO2006/011128
PCT Pub. Date: Feb. 2, 2006

(65) Prior Publication Data
US 2008/0275352 A1    Nov. 6, 2008

Related U.S. Application Data

(63) Continuation-in-part of application No. 10/893,570, filed on Jul. 15, 2004, now Pat. No. 7,998,080, which is a continuation-in-part of application No. PCT/IL2003/00042, filed on Jan. 15, 2003.

(60) Provisional application No. 60/348,278, filed on Jan. 15, 2002.

(51) Int. Cl.
*A61B 5/02* (2006.01)
*A61B 5/04* (2006.01)

(52) U.S. Cl. ........ 600/504; 600/506; 600/507; 600/382; 600/383; 600/393

(58) Field of Classification Search .................. 600/506, 600/504, 547, 372, 382, 383, 393
See application file for complete search history.

(56) References Cited

U.S. PATENT DOCUMENTS 4,308,873 A * 1/1982 Maynard ..................... 600/544
4,649,932 A    3/1987 Smith
(Continued)

FOREIGN PATENT DOCUMENTS
EP    0314088    5/1989
(Continued)

OTHER PUBLICATIONS

Weindling, A.M. et al, Effect of electrode sice on the contributions of intracranial and extracranial blood flow to the cerebral electrical impedance plethysmogram, Sep. 1982, Medical and Biological Engineering & Computing, 20, 545-549.*

(Continued)

*Primary Examiner* — Miranda Le
*Assistant Examiner* — Tiffany Weston
(74) *Attorney, Agent, or Firm* — Finnegan, Henderson, Farabow, Garrett & Dunner LLP.

(57) ABSTRACT

A method of estimating cerebral blood flow includes obtaining a measure of time-varying blood volume in the head, using an impedance plethysmography (102 and 104), obtaining a measure of time-varying blood volume in the scalp, and using the time-varying blood volume in the head and scalp to estimate cerebral blood flow.

16 Claims, 6 Drawing Sheets

U.S. PATENT DOCUMENTS

| | | | |
|---|---|---|---|
| 4,984,567 | A | 1/1991 | Kageyama et al. |
| 5,040,540 | A | 8/1991 | Sackner |
| 5,068,619 | A | 11/1991 | Nakano et al. |
| 5,265,615 | A | 11/1993 | Frank et al. |
| 5,282,840 | A | 2/1994 | Hudrlik |
| 5,353,802 | A | 10/1994 | Ollmar et al. |
| 5,396,893 | A | 3/1995 | Oberg et al. |
| 5,694,939 | A | 12/1997 | Cowings |
| 5,746,214 | A | 5/1998 | Brown et al. |
| 5,749,369 | A * | 5/1998 | Rabinovich et al. .......... 600/547 |
| 5,788,643 | A | 8/1998 | Feldman |
| 6,091,977 | A | 7/2000 | Tarjan et al. |
| 6,117,089 | A | 9/2000 | Sinha |
| 6,169,914 | B1 | 1/2001 | Hovland et al. |
| 6,223,069 | B1 | 4/2001 | Pfeiffer et al. |
| 6,245,027 | B1 | 6/2001 | Alperin |
| 6,413,223 | B1 | 7/2002 | Yang et al. |
| 6,491,647 | B1 | 12/2002 | Bridger et al. |
| 6,773,407 | B2 | 8/2004 | Yost et al. |
| 6,819,950 | B2 | 11/2004 | Mills |
| 6,832,113 | B2 | 12/2004 | Belalcazar |
| 6,875,176 | B2 | 4/2005 | Mourad et al. |
| 6,976,963 | B2 | 12/2005 | Clift |
| 6,996,428 | B2 | 2/2006 | Kislov et al. |
| 7,041,063 | B2 | 5/2006 | Abreu |
| 2004/0010185 | A1 | 1/2004 | Kimball et al. |
| 2004/0030258 | A1 | 2/2004 | Williams et al. |
| 2004/0034294 | A1 | 2/2004 | Kimball et al. |
| 2004/0049105 | A1 | 3/2004 | Crutchfield et al. |
| 2005/0054939 | A1 | 3/2005 | Ben-Ari et al. |
| 2006/0094964 | A1 | 5/2006 | Ragauskas et al. |
| 2006/0122523 | A1 | 6/2006 | Bonmassar et al. |
| 2006/0200033 | A1 | 9/2006 | Keren et al. |
| 2007/0287899 | A1 | 12/2007 | Poupko et al. |
| 2008/0004904 | A1 | 1/2008 | Tran |
| 2008/0021332 | A1 | 1/2008 | Brainard, III |
| 2008/0200787 | A1 | 8/2008 | Shapira et al. |
| 2009/0227881 | A1 | 9/2009 | Reichman et al. |

FOREIGN PATENT DOCUMENTS

| | | |
|---|---|---|
| EP | 1057498 | 12/2000 |
| GB | 1538695 | 1/1979 |
| JP | 03-118038 | 5/1991 |
| JP | 06-078888 | 3/1994 |
| JP | 2000-325324 | 11/2000 |
| JP | 2001-104274 | 4/2001 |
| JP | 2002-010986 | 1/2002 |
| JP | 2005-500116 | 1/2005 |
| RU | 2141249 | 11/1999 |
| WO | WO 96/16692 | 6/1996 |
| WO | WO 02/071923 | 9/2002 |
| WO | WO 02/087410 | 11/2002 |
| WO | WO 03/017834 | 3/2003 |
| WO | WO 03/059164 | 7/2003 |
| WO | WO 2006/006143 | 1/2006 |
| WO | WO 2006/011128 | 2/2006 |
| WO | WO 2006/134501 | 12/2006 |
| WO | WO 2008/072223 | 6/2008 |
| WO | WO 2006/087696 | 8/2008 |
| WO | WO 2010/041204 | 4/2010 |
| WO | WO 2010/041205 | 4/2010 |
| WO | WO 2010/041206 | 4/2010 |

OTHER PUBLICATIONS

Jevning, R, et al, Evaluation of consisitency among different electrical impedance indices of relative cerebral blood flow in normal resting individuals, Jan. 1988, Journal of Biomedical Engineering, vol. 11, 53-56.*

Official Action Dated Feb. 20, 2009 From the US Patent and Trademark Office Re.: U.S. Appl. No. 10/893,570.

Braunfels et al. "A Randomized, Controlled Trial of the Efficacy of Closed Chest Compressions in Ambulances", Preshop Emrge Care, 1(3): 128-131, 1997.

Grönlund et al. "High Frequency Variability of Trancephalic Electrical Impedance. A New Parameter for Monitoring of Neonatal Cerebral Circulation?", Proceedings of the Annual International Conference of the Engineering in Medicine and Biology Society, 6: 2513-2515, p. 2513, r-h col., Line 6-20. 1992.

Grönlund et al. "Trancephalic Electrical Impedance Provides a Means for Quantifying Pulsatile Cerebral Blood Volume Changes Following Head-Up Tilt", Early Human Development, 47: 11-18, 1997.

Ragauskas et al. "Implement of Non-Invasive Brain Physiological Moniitoring Concepts", Medical Engineering & Physics 25: 667-678, 2003.

Seipel et al. "Rheoencephalographic and Other Studies of Betahistine in Humans: I. The Cerebral and Peripheral Circulatory Effects of Single Doses in Normal Subjects", The Journal of Clinical Pharmacology, 15: 144-154, 1975.

Traczewski et al. "The Role of Computerized Rheoencephalography in the Assessment of Normal Pressure Hydrocephalus",Journal of Neutrotrauma, 22 (7): 836-843, 2005.

Webster "Measurement of Flow and Volume of Blood", Medical Instrumentation: Appliccation and Design: 332-371, 1997.

Response Dated Jan. 12, 2011 to Telephone Conference With Examiner of Jan. 12, 2011 From the International Bureau of WIPO Re. Application No. PCT/IB2009/054388.

Bonmassar et al. "The Spape of Electrical Impedance Spectroscopy (EIS) Is Altered in Stroke Patients", Proceedings of the 26th Annual International Conference of the IEEE EMBS, San Francisco, CA, USA, Sep. 1-5, 2005, p. 3443-3446, 2005.

Grönlund et al. "High Frequency Variability of Transcephalic Electrical Impedance—A New Parameter for Monitoring of Neonatal Cerebral Circulation", IEEE, p. 2513-2515.

Moshkalenko et al. "Slow Rhythmic Oscillations With the Human Cranium: Phenomenology, Origin, and Informational Significance", Human Physiology, 27(2): 171-178, 2001. Translated From Fiziologiya Cheloveka, 27(2): 47-55, 2001.

Ragauskas et al. "Implementation of Non-Invasive Brain Physiological Monitoring Concepts", Medical Engineering & Physics, 25: 667-678, 2003.

Weindling et al. "Effect of Electrode Size on the contributions of Intracranial and Extracranial Blood Flow to the Cerebral Electrical Impedance Plethysmogram", Medical & Biological Engineering & Computing, 20: 545-549, Sep. 1982.

Office Action Dated Sep. 5, 2008 From the Patent Office of the People's Republic of China Re.: Application No. 200580031088.2 and Its Translation Into English.

Office Action Dated May 23, 2008 From the Patent Office of the People's Republic of China Re.: Application No. 100580031089.7.

Official Action Dated Mar. 18, 2008 From the US Patent and Trademark Office Re.: U.S. Appl. No. 10/893,570.

Official Action Dated Sep. 19, 2008 From the US Patent and Trademark Office Re.: U.S. Appl. No. 10/893,570.

Response Dated May 5, 2010 to Rejection Decision of Feb. 12, 2010 From the State Intellectual Property Office of the People's Republic of China Re.: Application No. 200580031089.7.

González et al. "A Theoretical Study on Magnetic Induction Frequency Dependence of Phase Shift in Oedema and Haematoma", Physiological Measurement, 27: 829-838, 2006.

Grönlund et al. "High Frequency Variability of Transcephalic Electrical Impedance. A New Parameter for Monitoring of Neonatal Cerebral Circulation?", Proceedings of the Annual International Conference of the Engineering in Medicine and Biology Society, 6(Conf. 14): 2513-2515, 1992. p. 2513, r-h col., Lines 6-20.

Grönlund et al. "Transephalic Electrical Impedance Provides a Means for Quantifying Pulsatile Cerebral Blood Volume Changes Following Head-Up Tilt", Early Human Development, 47: 11-18, 1997.

Lovett Doust et al. "Aspects of the Cerebral Circulation During Non-REM Sleep in Healthy Controls and Psychiatric Patients, as Shown by Rheoencephalography", Psychophysiology, XP002572590, 12(5): 493-498, 1975. Abstract, p. 494, r-h col., § 2—p. 495, 1-h col., § 5, p. 495, 1-h col., § 1, p. 495, 1-h col., § 5—r-h col., § 1, p. 496, 1-h col., Fig. 1, Tables 1-2.

Seoane Martinez "Electrical Bioimpedance Cerebral Monitoring: Fundamental Steps Toward Clinical Applications", Thesis for the Degree of Doctor of Philosophy, Department of Signals and Systems, Division of Biomedical Engineering, Chalmers University of Technology, Göteborg, Sweden & School of Engineering, University College of Borås, Borås, Sweden, 153 P., 2007.
Response Dated Jul. 26, 2010 to the Written Opinion of Dec. 23, 2009 From the International Searching Authority Re.: Application No. PCT/IB2009/054394.
Official Action Dated Nov. 27, 2009 From the US Patent and Trademark Office Re.: U.S. Appl. No. 10/893,570.
Abboud et al. "Left-Right Asymmetry of Visual Evoked Potentials in Brain-Damaged Patients: A Mathematical Model and Experimental Results", Annals of Biomedical Engineering, XP000578781, 24(1): 75-86, Jan. 1, 1996. Abstract, Fig. 1.
Response Dated Oct. 3, 2010 to Communication Pursuant to Article 94(3) EPC of Jun. 2, 2010 From the European Patent Office Re. Application No. 05752203.9.
Response Dated Jan. 20, 2011 to Official Action of Nov. 5, 2010 From the US Patent and Trademark Office Re.: U.S. Appl. No. 10/893,570.
International Preliminary Report on Patentability Dated Jan. 21, 2011 From the International Preliminary Examining Authority Re. Application No. PCT/IB2009/054388.
Response Dated Sep. 1, 2010 to Official Action of Jun. 1, 2010 From the US Patent and Trademark Office Re.: U.S. Appl. No. 10/893,570.
Communication Pursuant to Article 94(3) EPC Dated Apr. 3, 2009 From the European Patent Office Re.: Application No. 05750856.6.
Communication Pursuant to Article 94(3) EPC Dated Feb. 24, 2010 From the European Patent Office Re.: Application No. 07827394.3.
Communication Pursuant to Article 94(3) EPC Dated Mar. 29, 2010 From the European Patent Office Re.: Application No. 05750856.6.
Rejection Decision Dated Feb. 12, 2010 From the State Intellectual Property Office of the People's Republic of China Re.: Application No. 200580031089.7 and Its Translation Into English.
Response Dated Mar. 1, 2010 to Official Action of Nov. 27, 2009 From the US Patent and Trademark Office Re.: U.S. Appl. No. 10/893,570.
Supplementary European Search Report Dated Jan. 28, 2010 From the European Patent Office Re.: Application No. 05752203.9.
Barbosa-Silva et al. "Bioelectrical Impedance Analysis: Population Reference Values for Phase Angle by Age and Sex", The American Journal of Clinical Nutrition, 82: 49-52, 2005.
Jacquy et al. "Cerebral Blood Flow and Quantitative Rheoencephalography", Electroencephalographyand Clinical Neurophysiology, 37: 507-511, 1974.
Jevning et al. "Evaluation of Consistency Among Different Electrical Impedance Indices of Relative Cerebral Blood Flow in Normal Resting Individuals", Journal of Biomedical Engineering, XP022444925, 11(1): 53-56, Jan. 1, 1989.
Keren et al. "Evaluation of an Noninvasive Continuous Cardiac Output Monitoring System Based on Thoracic Bioreactance", American Journal of Physiology: Heart Circulation Physiology, 293: H583-H589, 2007.
Steiner et al. "Continuous Monitoring of Cerebrovascular Pressure Reactivity Allows Determination of Optimal Cerebral Perfusion Pressure in Patients With Traumatic Brain Injury", Critical Care Medicine, 30(4): 733-738, Apr. 2002. Abstract.
Stiefel et al. "Reduced Mortality Rate in Patients With Severe Traumatic Brain Injury Treated With Brain Tissue Oxygen Monitoring", Journal of Neurosurgery, 103(5): 805-811, Nov. 2005.
Communication Pursuant to Article 94(3) EPC Dated Jun. 2, 2010 From the European Patent Office Re. Application No. 05752203.9.
Official Action Dated Jun. 1, 2010 From the US Patent and Trademark Office Re.: U.S. Appl. No. 10/893,570.
Official Action Dated Nov. 5, 2010 From the US Patent and Trademark Office Re.: U.S. Appl. No. 10/893,570.
Response Dated Jul. 18, 2010 to Communication Pursuant to Article 94(3) EPC of Feb. 24, 2010 From the European Patent Office Re.: Application No. 07827394.3.
Response Dated Jul. 19, 2010 to Communication Pursuant to Article 94(3) EPC of Mar. 29, 2010 From the European Patent Office Re.: Application No. 05750856.6.
Translation of Office Action Dated Jun. 5, 2009 From the State Intellectual Property Office of the People's Republic of China Re.: Application No. 200680029920.X.

Translation of Office Action Dated Aug. 7, 2009 From the State Intellectual Property Office of the People's Republic of China Re.: Application No. 200580031089.7.
Letter in Reponse Dated Dec. 7, 2010 to Telephone Conference With Examiner of Dec. 7, 2010 From the International Bureau of WIPO Re. Application No. PCT/IB2009/054392.
Letter in Reponse Dated Dec. 7, 2010 to Telephone Conference With Examiner of Dec. 7, 2010 From the International Bureau of WIPO Re. Application No. PCT/IB2009/054394.
Translation of Notificiation of Reasons for Rejection Dated Dec. 14, 2010 From the Japanese Patent Office Re. Application No. 2007-520969.
International Preliminary Report on Patentability Dated Dec. 21, 2010 From the International Preliminary Examining Authority Re. Application No. PCT/IB2009/054392.
International Preliminary Report on Patentability Dated Dec. 27, 2010 From the International Preliminary Examining Authority Re.: Application No. PCT/IB2009/054394.
Bellner et al. "Transcranial Doppler Sonography Pulsatility Index (PI) Reflects Intracranial Pressure (ICP)", Surgical Neurology, 62(1): 45-51, Jul. 2004.
Czosnyka "Cerebral Perfusion in Head-Injured Patients: A Nonivasive Assessment Using Transcranial Doppler Ultrasonography", Journal of Neurosurgery, 88: 802-808, 1998.
Wintermark et al. "Comparatibe Overview of Brain Perfusion Imaging Techniques", Stroke, vol. 36e, p. 83-99, 2005.
Response Dated Aug. 9, 2010 to the Written Opinion of Apr. 20, 2010 From the International Searching Authority Re.: Application No. PCT/IB2009/054392.
Response Dated Jul. 29, 2010 to the Written Opinion of Apr. 20, 2010 From the International Searching Authority Re.: Application No. PCT/IB2009/054388.
International Preliminary Report on Patentability Dated Jan. 3, 2008 From the International Bureau of WIPO Re.: Application No. PCT/IB2006/050174.
International Preliminary Report on Patentability Dated Nov. 15, 2006 From the International Preliminary Examining Authority Re.: Application No. PCT/IL2005/000631.
International Preliminary Report on Patentability Dated May 23, 2007 From the International Preliminary Examining Authority Re.: Application No. PCT/IL05/00632.
International Preliminary Report on Patentability Dated Mar. 26, 2009 From the International Preliminary Examining Authority Re.: Application No. PCT/IL2007/001421.
International Search Report Dated Oct. 14, 2003 From the International Searching Authority Re.: Application No. PCT/IL03/00042.
Written Opinion Dated Dec. 5, 2005 From the International Searching Authority Re.: Application No. PCT/IL05/000632.
Written Opinion Dated Oct. 20, 2005 From the International Searching Authority Re.: Application No. PCT/IL2005/000631.
Restriction Official Action Dated Dec. 13, 2011 From the US Patent and Trademark Office Re. U.S. Appl. No. 11/610,553.
Translation of Notification to Grant Patent Right for Invention Dated May 26, 2011 From the State Intellectual Property Office of the People's Republic of China Re. Application No. 200780051314.2.
Communication Pursuant to Article 94(3) EPC Dated Jun. 22, 2011 From the European Patent Office Re.: Application No. 07827394.3.
Translation of Notice of Reason for Rejection Dated Jun. 17, 2011 From the Japanese Patent Office Re. Application No. 2008-516457.
Official Action Dated Jun. 7, 2011 From the US Patent and Trademark Office Re. U.S. Appl. No. 11/572,157.
Bartocci et al. "Cerebral Blood-Flow Monitor for Use in Neonatal Intensive Care Units", Computer Methods and Programs in Biomedicine, 59: 61-73, 1999.
Colditz et al. "Continuous Cerebral Electrical Impedance Monitoring in Sick Preterm Infants", European Journal of Pediatrics, 149: 428-431, 1990.
Linderholm et al. "Imicroelectrical Impedance Tomography for Biophysical Characterization of Thin Film Biomaterials", Transducer '03, The 12th International Conference on Solid State Sensors, Actuators and Microsystems, Boston, Jun. 8-12, 2003, p. 284-287, Jun. 2003.

Response Dated Sep. 5, 2011 to Notice of Reason for Rejection of Jun. 17, 2011 From the Japanese Patent Office Re. Application No. 2008-516457.

Decision to Grant a European Patent Pursuant to Article 97(1) EPC Dated Nov. 10, 2011 From the European Patent Office Re.: Application No. 05752203.9.

International Preliminary Report on Patentability Dated Apr. 21, 2011 From the International Bureau of WIPO Re. Application No. PCT/IB2009/054388.

Response Dated Feb. 27, 2011 to Office Action of Aug. 12, 2010 From the State Intellectual Property Office of the People's Republic of China Re. Application No. 200780051314.2.

Translation of Office Action Dated Aug. 12, 2010 From the State Intellectual Property Office of the People's Republic of China Re. Application No. 200780051314.2.

Communication Pursuant to Article 94(3) EPC Dated Apr. 28, 2011 From the European Patent Office Re. Application No. 05752203.9.

Communication Under Rule 71(3) EPC Dated May 18, 2011 From the European Patent Office Re.: Application No. 05750856.6.

Response Dated May 31, 2011 to Notification of Reasons for Rejection of Dec. 14, 2010 From the Japanese Patent Office Re. Application No. 2007-520969.

Decision of Rejection Dated Jul. 28, 2011 From the Japanese Patent Office Re. Application No. 2007-520969 and Its Translation Into English.

Response Dated Jul. 19, 2011 to Notification of Reasons for Rejection of Mar. 22, 2011 From the Japanese Patent Office Re. Application No. 2007-520968.

Response Dated Oct. 27, 2011 to Communication Pursuant to Article 94(3) EPC of Jun. 22, 2011 From the European Patent Office Re.: Application No. 07827394.3.

Response Dated Oct. 27, 2011 to Communication Pursuant to Article 94(3) EPC of Apr. 28, 2011 From the European Patent Office Re. Application No. 05752203.9.

Response Dated Nov. 7, 2011 to Official Action of Jun. 7, 2011 From the US Patent and Trademark Office Re. U.S. Appl. No. 11/572,157.

Response Dated Nov. 16, 2011 to Decision of Rejection of Jul. 28, 2011 From the Japanese Patent Office Re. Application No. 2007-520969.

Official Action Dated Dec. 19, 2011 From the US Patent and Trademark Office Re. U.S. Appl. No. 11/572,157.

Restriction Official Action Dated Jan. 6, 2012 From the US Patent and Trademark Office Re. U.S. Appl. No. 11/921,937.

Costeloe et al. "A Comparison Between Electrical Impedance and Strain Gauge Plethysmography for the Study of Cerebral Blood Flow in the Newborn", Pediatric Research, 18(3): 290-295, Mar. 1984.

Hua et al. "Using Compound Electrodes in Electrical Impedance Tomography", IEEE Transactions on Biomedical Engineering, 40(1): 29-34, Jan. 1993.

Weindling et al. "Cerebral Haemodynamics in Newborn Babies Studied by Electrical Impedance", Acta Paediatrica Scandinavica Supplement, 311: 14-19, 1983.

Translation of Notification of Reasons for Rejection Dated Mar. 22, 2011 From the Japanese Patent Office Re. Application No. 2007-520968.

Notice of Allowance Dated Apr. 11, 2011 From the US Patent and Trademark Office Re.: U.S. Appl. No. 10/893,570.

\* cited by examiner

CEREBRAL PERFUSION MONITOR

RELATED APPLICATIONS

The present application is a U.S. national phase of PCT/IL05/000632, filed on Jun. 15, 2005 and published as WO 2006/011128 on Feb. 2, 2006, which is a continuation-in-part of U.S. patent application Ser. No. 10/893,570, filed Jul. 15, 2004, which is a continuation-in-part of PCT patent application PCT/IL03/00042, filed Jan. 15, 2003, which claims benefit under 35 USC 119(e) from U.S. provisional patent application 60/348,278, filed Jan. 15, 2002. PCT/IL05/000632 is related to PCT/IL05/000631, also filed on Jun. 15, 2005, and published as WO 2006/006143 on Jan. 19, 2006. The disclosures of all of these applications are incorporated herein by reference.

FIELD OF THE INVENTION

The field of the invention relates to measuring blood flow in the head.

BACKGROUND OF THE INVENTION

There is a need to measure cerebral blood flow during various medical events and procedures, because any disturbance to the flow of blood to the brain may cause injury to the function of the brain cells, and even death of brain cells if the disturbance is prolonged. Maintaining blood flow to the brain is especially important because brain cells are more vulnerable to a lack of oxygen than other cells, and because brain cells usually cannot regenerate following an injury.

A number of common situations may cause a decrease in the general blood flow to the brain, including arrhythmia, myocardial infarction, and traumatic hemorrhagic shock. A sudden increase in blood flow to the brain may also cause severe damage, and is especially likely to occur in newborn or premature babies, although such an increase may also occur in other patients with certain medical conditions, or during surgery. In all these cases, data regarding the quantity of blood flow in the brain, and the changes in flow rate, may be important in evaluating the risk of injury to the brain tissue and the efficacy of treatment. The availability of such data may enable the timely performance of various medical procedures to increase, decrease, or stabilize the cerebral blood flow, and prevent permanent damage to the brain.

In the absence of a simple means for direct and continuous monitoring of cerebral blood flow, information about changes in cerebral blood flow is inferred indirectly by monitoring clinical parameters which can be easily measured, such as blood pressure. But due to the different relation between blood pressure and cerebral blood flow in different medical conditions, there may be situations in which cerebral blood flow is inadequate even when blood pressure appears to be adequate. Cerebral blood flow may also be inferred indirectly by monitoring neurological function, but since neurological dysfunction is often irreversible by the time it is detected, it is more desirable to detect changes in cerebral blood flow directly, while its effects on brain function are still reversible.

Existing means for measuring cerebral blood flow are complex, expensive, and in some cases invasive, which limits their usefulness. Three methods that are presently used only in research are 1) injecting radioactive xenon into the cervical carotid arteries and observing the radiation it emits as it spreads throughout the brain; 2) positron emission tomography, also based on the injection of radioactive material; and 3) magnetic resonance angiography, performed using a room-sized, expensive, magnetic resonance imaging system, and requiring several minutes to give results. These three methods can only be carried out in a hospital or other center that has the specialized equipment available, and even in a hospital setting it is not practical to monitor patients continuously using these methods.

A fourth method, trans-cranial Doppler (TCD) uses ultrasound, is not invasive and gives immediate results. However, TCD fails to give a correct determination of blood flow in about 15% of patients, due to the difficulty of passing sound waves through the cranium, and it requires great skill by professionals who have undergone prolonged training and practice in performing the test and deciphering the results. Another disadvantage of TCD is that it measures only regional blood flow in the brain, and does not measure global blood flow. Doppler ultrasound may also be used to measure blood flow in the carotid arteries, providing an estimate of blood flow to the head, but not specifically to the brain, and not including blood flow to the head through the vertebral arteries, which is difficult to measure by ultrasound because of their proximity to the vertebrae.

Two additional techniques that are used, generally in research, to measure blood flow in the head and in other parts of the body are electric impedance plethysmography (IPG) and photoplethysmography (PPG). U.S. Pat. No. 6,819,950, to Mills, describes the use of PPG to detect carotid stenosis, among other conditions. U.S. Pat. No. 5,694,939, to Cowings, describes biofeedback techniques for controlling blood pressure, which include the use of IPG in the lower leg and PPG in the finger. U.S. Pat. No. 5,396,893, to Oberg et al, states that PPG is superior to IPG for monitoring patients' cardiac and respiration rates. U.S. Pat. No. 6,832,113, to Belalcazar, describes the use of either IPG or PPG to measure blood flow, for purposes of optimizing a cardiac pacemaker. U.S. Pat. No. 6,169,914, to Hovland et al, describes the use of various types of sensors, including IPG and PPG, for monitoring female sexual arousal with a vaginal probe, and describes using different types of sensors in combination.

U.S. Pat. No. 6,413,223, to Yang et al, describes a probe, used on the finger, which contains two PPG sensors and one IPG sensors. The combined data from the three sensors, analyzed using a mathematical model of arterial blood flow, provides a more accurate measurement of blood flow than would be obtained by using IPG or PPG alone.

J. H. Seipel and J. E. Floam, in J. Clinical Pharmacology 15, 144-154 (1975) present the results of a clinical study of the effects of a drug, betahistidine, on cerebral, cranial, scalp and calf blood circulation. Rheoencephalography (REG), a form of IPG, was used to measure the amplitude of cerebral blood flow.

The disclosures of all of the above mentioned patents and publication are incorporated herein by reference.

SUMMARY OF THE INVENTION

An aspect of some embodiments of the invention relates to estimating cerebral blood flow, by 1) using IPG to obtain a measure of the combined change in cerebral and possibly including scalp blood volume during a cardiac cycle; 2) using PPG or another method, including surface IPG or ultrasonics, to obtain a measure of the change mainly in scalp blood volume; and 3) combining the two measurements to find the change in cerebral blood volume. The cerebral blood flow is then optionally found from the time derivative of the cerebral blood volume. Since there is generally a component of cerebral blood flow that is not associated with varying cerebral blood volume, in addition to a component associated with the variation in cerebral blood volume over a cardiac cycle, using the time derivative of the cerebral blood volume may only give an indication of the relative cerebral blood flow, rather than the absolute cerebral blood flow.

Optionally, the time-varying part of the cerebral blood volume is found by subtracting a weighted or normalized PPG signal from the IPG signal, to obtain a measure that depends primarily on the time-varying part of the cerebral blood volume, with relatively little dependence on the time-varying part of the scalp blood volume. Optionally, the weighting factor is estimated by using the fact that there is a time delay between the cerebral blood flow and the scalp blood flow, in each cardiac cycle, and assuming that in a later part of each cardiac cycle, for example the last third of each cycle, when the blood pressure is decreasing, the IPG signal is dominated by the time-varying part of the scalp blood volume. Alternatively or additionally, the weighting factor is estimated by using the power spectra and cross-power spectrum of the IPG and PPG signals. For example, the cross-power spectrum is used to find a range of frequencies for which the IPG and PPG signals are similar, and the weighting factor is set equal to the square root of the ratio between the power spectrum of the IPG signal integrated over those frequencies, and the power spectrum of the PPG signal integrated over those frequencies.

Optionally, the IPG measurement is made by placing IPG electrode units on two sides of the head, for example on the left and right temples. Optionally, one or both of the IPG electrode units is combined with a PPG sensor, in a single unit. Optionally, the IPG electrode units include separate current-carrying and voltage-measuring electrodes. For example, the current-carrying electrode may be in the form of a concentric ring surrounding the voltage-measuring electrode, or vice versa.

An aspect of some embodiments of the invention relates to estimating cerebral blood flow by using characteristics of the IPG signal alone. For example, the cerebral blood flow is estimated from the peak value of the IPG signal in each cardiac cycle, or from the peak rate of rise of the IPG signal after the beginning of each cardiac cycle, or from the height of the first local peak or inflection point in the IPG signal after the beginning of each cardiac cycle. The beginning of each cardiac cycle is defined, for example, by the peak of the R-wave of an ECG, or by the time of the minimum in the IPG or PPG signal, or by the time of the diastolic pressure. The rapid initial rate of rise in the IPG signal, up to the peak or up to the first local peak or inflection point, may be dominated by the cerebral blood flow, even if the IPG signal during the rest of the cardiac cycle is largely influenced by the scalp blood volume, since the scalp blood volume, as indicated by PPG data, generally rises more slowly, and with a delay, at the beginning of each cardiac cycle. Optionally, PPG data is also obtained, to confirm that the scalp blood volume is rising slowly initially, and that the rapid initial rise of the IPG signal is indeed due mostly to the cerebral blood flow.

Some embodiments of the invention may be particularly useful for monitoring premature infants, for example those with weight under 1.5 kg, who generally have poor ability to maintain constant blood flow to the brain due to the immaturity of their cerebral blood flow autoregulation system. Abrupt changes in blood flow to the brain can be caused by changes in respiration, changes in blood pressure, and manipulation of the infants by medical staff. Such abrupt changes in cerebral blood flow, if not immediately detected and treated, can cause severe brain injury, including injuries caused by cerebral hemorrhage which occurs in 10% to 30% of premature babies. The invention may also be useful in monitoring mature babies who may be at risk of brain hemorrhage or ischemia for various reasons.

The invention may also be useful for monitoring cerebral blood flow in 1) patients undergoing surgery of the carotid arteries, in which a clamp is applied to one of the carotids, potentially reducing blood flow to the brain; 2) patients with stenosis or occlusion of the carotid arteries or cerebral arteries, particularly if they are undergoing procedures such as intra-arterial catherization or stent application in the affected arteries; 3) brain injury patients, in whom brain edema might cause a decrease in blood perfusion, and herniation of the brain; 4) neurosurgery patients, during and for a few days after the surgery, when cerebral blood flow is often impaired; 5) patients undergoing other major surgery, including heart surgery, in which massive bleeding and resulting hypotension could lead to a decrease in cerebral blood flow. In all of these categories of patients, monitoring of cerebral blood flow could lead to prompt intervention before brain injury occurs.

An aspect of some embodiments of the invention relates to a probe including both electrical and scalp blood flow measurement sensors. Optionally, the probe is configured so that when placed at a certain (optionally pre-determined) location on the skull, for example, the temple, the blood flow measurement probe will be aimed at the vascular bed (e.g., source) of the location where electric field will be sensed.

There is thus provided in accordance with an exemplary embodiment of the invention, a method of estimating cerebral blood flow, comprising:
 a) obtaining a measure of time-varying blood volume in the head, using impedance plethysmography;
 b) obtaining a measure of time-varying blood volume in the scalp; and
 c) using the measure of time-varying blood volume in the head and time-varying blood volume in the scalp to estimate the cerebral blood flow.

Optionally, obtaining a measure of time-varying blood flow in the scalp comprises using photoplethysmography.

In an exemplary embodiment of the invention, estimating the cerebral blood flow comprises estimating the relative cerebral blood flow as it changes over time.

In an exemplary embodiment of the invention, using the measures of time-varying blood volume comprises finding a difference between weighted measures of time-varying blood volume.

In an exemplary embodiment of the invention, the measures of time-varying blood volume are weighted to have at least approximately the same value at a time in the cardiac cycle when the blood pressure is falling.

In an exemplary embodiment of the invention, the measures of time-varying blood volume are weighted to have approximately equal power spectra at frequencies for which the cross-power spectrum between the measures of time-varying blood volume is relatively high.

In an exemplary embodiment of the invention, obtaining a measure of blood volume in the head using impedance plethysmography comprises:
 a) passing a current through the head using two current-carrying electrodes; and
 b) measuring a voltage across the head, associated with the current, using two voltage-measuring electrodes.

Optionally, the method includes applying to the head an annular electrode surrounding at least one of the current-carrying electrodes, and maintaining the annular electrode at a same voltage as the current-carrying electrode it surrounds, thereby suppressing radial current from said current-carrying electrode.

Alternatively or additionally, the voltage-measuring electrodes are distinct from, and substantially electrically decoupled from, the current-carrying electrodes.

In an exemplary embodiment of the invention, obtaining a measure of blood volume in the head using impedance plethysmography comprises placing the two current-carrying electrodes on the left and right temples respectively.

In an exemplary embodiment of the invention, obtaining a measure of blood volume in the head using impedance plethysmography comprises placing each of the two voltage-measuring electrodes on the head in a position adjacent to a different one of the current-carrying electrodes. Optionally, obtaining a measure of blood volume in the scalp using photoplethysmography comprises placing a photoplethysmography sensor on the head adjacent to one of the current-carrying electrodes and to the voltage-measuring electrode which is adjacent to said current-carrying electrode.

There is also provided in accordance with an exemplary embodiment of the invention, a method of estimating cerebral blood flow, comprising:
 a) measuring an impedance across the head as a function of time in a cardiac cycle; and
 b) estimating the cerebral blood flow from a rate of change of the impedance during a time in the cardiac cycle when the blood pressure is rising.

There is also provided in accordance with an exemplary embodiment of the invention, a unit for estimating cerebral blood flow, adapted for placing on the head, the unit comprising:
 a) at least one electrode adapted for impedance plethysmography; and
 b) a plethysmography sensor adapted for measuring blood flow in a scalp.

Optionally, the sensor is a photoplethysmography sensor.

In an exemplary embodiment of the invention, the unit comprises a signal processor configured to process one or both of data from the photoplethysmography sensor and impedance plethysomography data from the electrode.

In an exemplary embodiment of the invention, the at least one electrodes comprise:
 a) a current-carrying electrode adapted for injecting current through the head when it is placed on the skin; and
 b) a voltage-measuring electrode adapted for measuring voltage across the head when it is placed on the skin, and when the current-carrying electrode is injecting current.

In an exemplary embodiment of the invention, the current-carrying and voltage-measuring electrodes are configured such that the voltage measuring electrode will measure a potential substantially equal to a potential at the dermis, largely excluding the voltage drop across the epidermis, when the current-carrying electrode is injecting current.

In an exemplary embodiment of the invention, the unit is adapted for use in patients of a range of degree of maturity, wherein the current-carrying electrode comprises an annulus surrounding the voltage-measuring electrode, and the radial thickness of the annulus and the gap between the current-carrying and voltage-measuring electrodes are each at least twice as great as a typical thickness of the epidermis in patients of said range of degree of maturity.

In an exemplary embodiment of the invention, the radial thickness of the annulus and the gap between the current-carrying and voltage-measuring electrodes are each at least 1 mm.

In an exemplary embodiment of the invention, the radial thickness of the annulus and the gap between the current-carrying and voltage-measuring electrodes are each at least 2 mm.

In an exemplary embodiment of the invention, the unit includes an annular electrode surrounding the current-carrying electrode, thereby suppressing radial current from the current-carrying electrode when the annular electrode is maintained at the same voltage as the current-carrying electrode.

There is also provided in accordance with an exemplary embodiment of the invention, a system for estimating cerebral blood flow, comprising:
 a) at least one unit as described herein;
 b) an impedance measuring unit comprising at least one electrode adapted for placing on the head and performing impedance plethysmography;
 c) a power supply adapted for passing current across the head between one of the at least one electrodes of the one unit and one of the at least one electrodes of the impedance measuring unit, when said units are placed on different sides of the head; and
 d) a data analyzer which calculates a cerebral blood flow using impedance data obtained from a voltage difference measured between one of the at least one electrodes of the one unit and one of the at least one electrodes of the impedance measuring unit, and from photoplethysmography data generated by the photoplethysmography sensor.

Optionally, the impedance measuring unit is also a unit as described herein.

BRIEF DESCRIPTION OF THE DRAWINGS

Exemplary embodiments of the invention are described in the following sections with reference to the drawings. The drawings are not necessarily to scale and the same reference numbers are generally used for the same or related features that are shown on different drawings.

FIG. 8 shows a schematic plot of an IPG signal and its time derivative as a function of time, illustrating a method of

DETAILED DESCRIPTION OF EXEMPLARY EMBODIMENTS

Figure 1A:
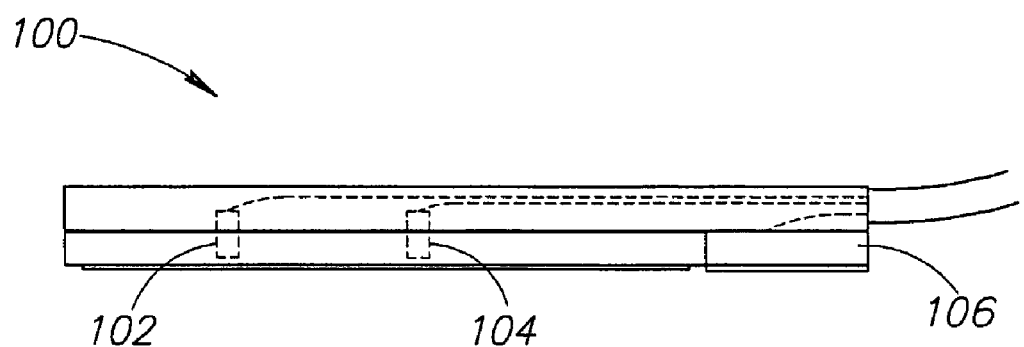
FIGS. 1A, 1B and 1C show schematic views, respectively from the side, the back, and the face, of a unit combining IPG electrodes and a PPG sensor, according to an exemplary embodiment of the invention.
Figure 1B:
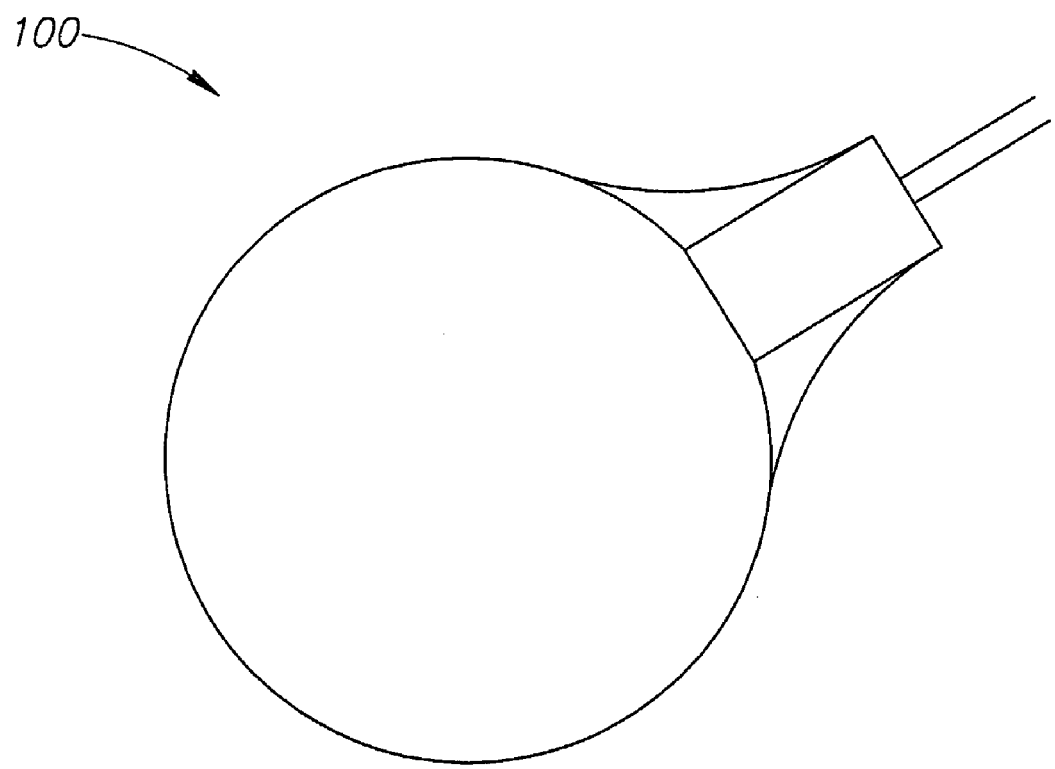
Figure 1C:
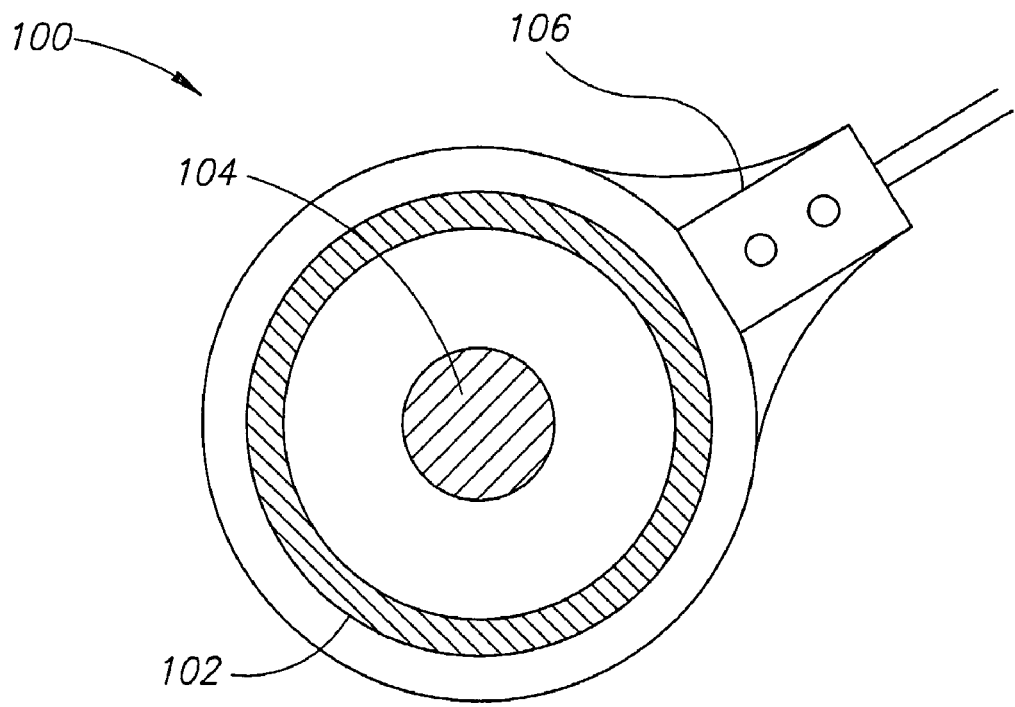
Figure 2:
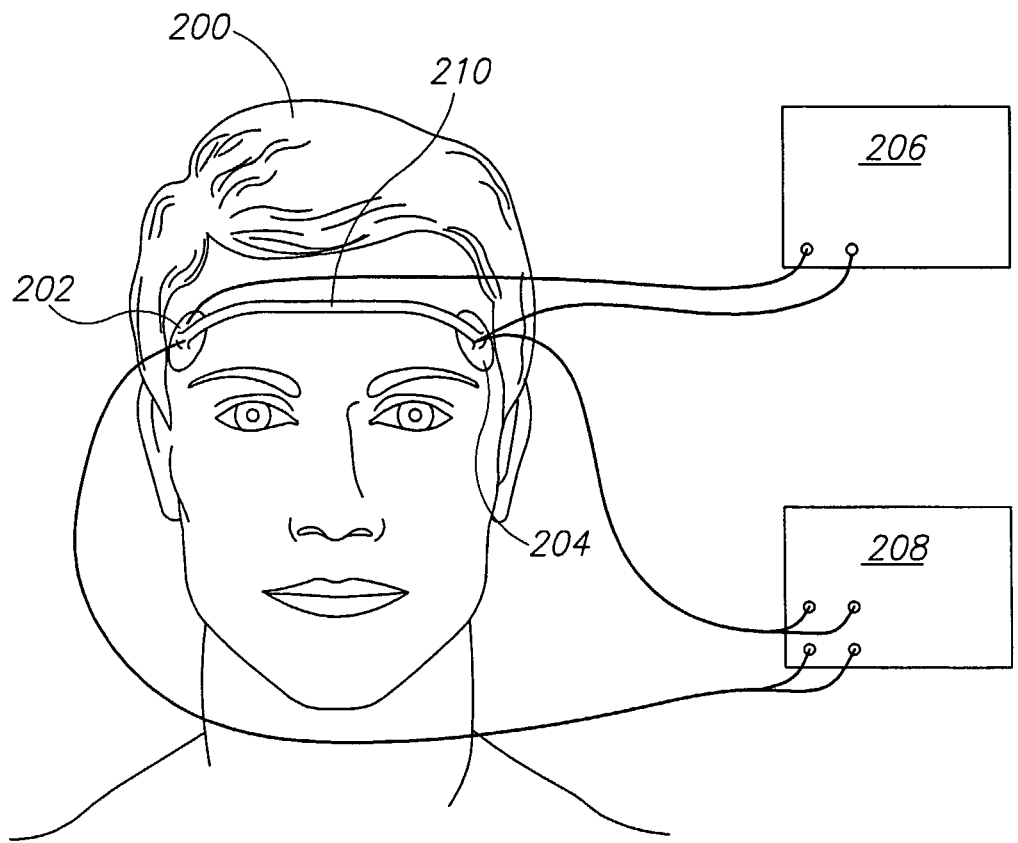
FIG. 2 is a schematic perspective view showing placement on the temples of the units shown in FIGS. 1A-1C, according to an exemplary embodiment of the invention.

FIGS. 1A, 1B, and 1C respectively show side, back, and face views of a unit 100 which optionally combines a current electrode 102 and a voltage electrode 104 for impedance plethysmography (IPG), and a sensor 106 for photoplethysmography (PPG), according to an exemplary embodiment of the invention. The face side of unit 100, shown in FIG. 1C, is the side that is placed against the skin, as shown in FIG. 2. As shown in FIG. 2, two such units, placed for example on opposite sides of the head, are optionally used for IPG, passing current from one unit to the other and measuring the voltage between them. For reasons described below, alternating current is generally used.

PPG sensor 106 measures the color of the skin to determine a degree of perfusion of oxygenated blood in the skin adjacent to unit 100, as described, for example, by J. Webster, "Measurement of Flow and Volume of Blood," in John G. Webster (ed.), *Medical Instrumentation: Application and Design* (Wiley, 1997), the disclosure of which is incorporated herein by reference. Optionally, PPG sensor 106 incorporates a digital signal processor which converts the raw sensor signal into a usable output signal. Optionally, unit 100 also includes a digital signal processor which processes voltage and/or current and/or photo reflection data of the electrodes and/or PPG in one or both units. Alternatively, the raw signal from sensor 106 and/or data from the electrodes is processed partly or entirely by an external signal processor not located in unit 100.

Alternatively, instead of having separate current and voltage electrodes, unit 100 has a single electrode, used both for carrying current and for measuring voltage. However, using separate electrodes for carrying current and measuring voltage has the potential advantage that the measured voltage may not be very sensitive to a high contact resistance between the electrodes and the skin, or to a high resistance across the epidermis, one or both of which can dominate the voltage drop between the current electrodes on opposite sides of the head. The contact resistance and the epidermis resistance have little or no dependence on blood flow, so it is generally desirable for the IPG signal not to be sensitive to the contact and epidermis resistance. This goal is optionally achieved by using an annular shape for current-electrode 102, and locating voltage-electrode 104 in the center of the annulus, but substantially electrically decoupled from it. The radial thickness of the annulus of electrode 102, and the gap between electrodes 102 and 104, are optionally at least somewhat greater than the thickness of the epidermis under the electrodes, for example at least twice as great. Optionally, the radial thickness of the annulus of electrode 102 is at least 2 mm, or at least 5 mm, or at least 1 cm. Optionally, the gap between electrodes 102 and 104 is at least 2 mm, or at least 5 mm, or at least 1 cm, or intermediate or smaller values.

With this geometry of electrodes 102 and 104, and with current-electrode 102 making good contact with the skin over the surface of the electrode, the current across the epidermis will be broadly distributed, compared to the thickness of the epidermis. The high electric field in the high resistivity epidermis will be largely confined to the region under the current electrode, with a much lower fringing field reaching voltage measuring electrode 104. But the potential in the much lower resistivity dermis will be fairly uniform under unit 100, and the potential of electrode 104 will be close to this potential. The same will be true under the unit on the other side of the head. The voltage difference between the two voltage electrodes 104 on the two sides of the head will be close to the difference in potential in the dermis under the two electrodes. For a given current, this potential difference depends on the impedance of the dermis of the temples and the scalp, and the impedance of the cranium and the brain, as described below in connection with FIG. 3, rather than on the impedance across the epidermis.

Figure 1D:
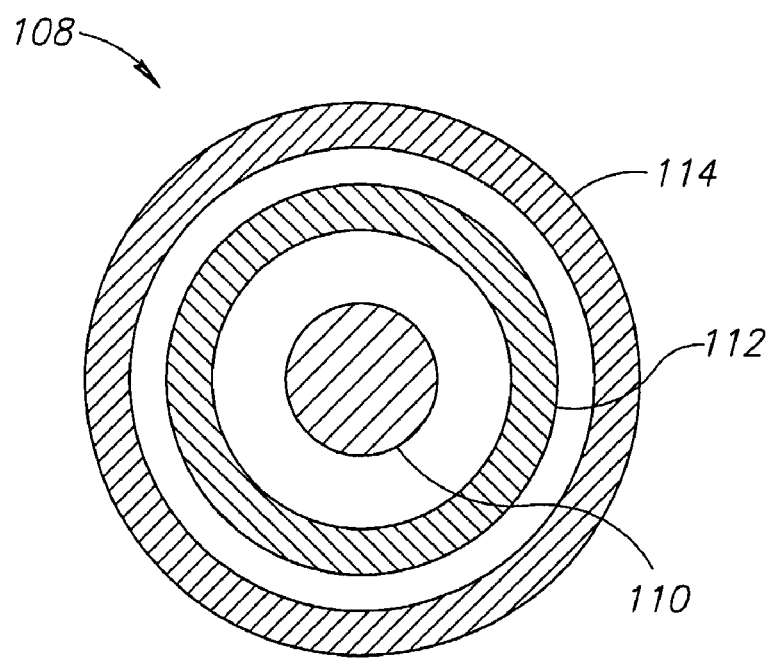
FIG. 1D is a schematic view of IPG electrodes according to another exemplary embodiment of the invention.

An alternative configuration 108 for the voltage and current electrodes is shown in FIG. 1D. Current is injected through electrode 110, located in the center, and voltage is measured at electrode 112, in the form of an annulus surrounding electrode 110, which is electrically well isolated from electrode 110. An additional electrode 114, also in the form of an annulus, surrounds electrode 112, and injects whatever current is necessary in order to remain at the same voltage as electrode 110. However, optionally, only the current injected through electrode 110 is considered for purposes of finding the impedance. With configuration 108, there will be very little radial electric field, and hence very little radial current flow, in the dermis under the region between electrodes 110 and 114. Hence, the current from electrode 110 will be directed mostly into the head, and relatively more of this current will flow through the brain as opposed to flowing through the scalp, while most of the current flowing through the scalp will be injected by electrode 114, and may be ignored for purposes of measuring the impedance. With this configuration, the impedance measurement will be more sensitive to the impedance of the brain, and less sensitive to the impedance of the scalp. Optionally, the thicknesses of electrodes 112 and 114, and the gaps between them and between electrodes 110 and 112, have the same possible dimensions as those mentioned above for electrodes 102 and 104.

Alternatively or additionally, the current through electrode 114 is also measured, and compared to the current through electrode 110, in order to estimate the ratio of the scalp path impedance to the cerebral path impedance. This ratio may be used to find a weighting factor to be used for the PPG signal when subtracting the PPG signal from the IPG signal, instead of or in addition to the methods described above for finding the weighting factor.

Alternatively, instead of the electrode configurations shown in FIGS. 1C and 1D, any of the electrode configurations described in U.S. patent application Ser. No. 10/893,570 is used, or any other electrode configuration is used in which the current electrode is adjacent to the voltage electrode. If the current electrode has dimensions that are large compared to the thickness of the epidermis, and the voltage electrode is separated from the current electrode by a similar distance, then the voltage electrode will measure a potential that tends to be close to the potential at the dermis under the voltage and current electrodes, largely excluding the voltage drop across the epidermis.

FIG. 2 shows a head 200 with units 202 and 204 placed on the temples on each side of the head, according to an exemplary embodiment of the invention. Optionally, each of units 202 and 204 is like unit 100 in FIGS. 1A-1C, including both IPG electrodes and PPG sensors. A power supply 206 passes current between the current-electrodes in units 202 and 204, and a voltage difference is measured between the voltage-electrodes in units 202 and 204, while PPG data is optionally supplied by the PPG sensors in both units. Alternatively, only one of units 202 and 204 has a PPG sensor combined with it, or only one of the PPG sensors is used, or neither unit has a PPG sensor combined with it and a separate PPG sensor is used. A data analyzer 208 uses the voltage difference between the voltage electrodes, together with the PPG data, to estimate the cerebral blood flow, as will be described below in the description of FIGS. 4 and 5.

Optionally, a C-shaped spring device 210 connects units 202 and 204, and provides a force to keep units 202 and 204 in place on the temples, similar to headphones. Alternatively, suction cups, such as those used for electrocardiographs, are used to keep units 202 and 204 in place on the temples, or any other method known in the art, for example an adhesive, is used to keep units 202 and 204 in place on the temples.

Alternatively, instead of placing units 202 and 204 on the temples, they are placed at other locations on the head, for example on the forehead and in the back of the head. Although the two electrodes need not be placed on opposite sides of the head, placing them on at least approximately opposite sides of the head has the potential advantage that relatively more current goes through the interior of the skull, rather than through the scalp. Placing the electrodes on the temples has the potential advantage that there is no need to shave the skin before placing the electrodes, and the skull is relatively thin at the temples, also causing relatively more of the current to go through the brain rather than through the scalp. Placing an electrode over one of the closed eyelids, or over the foramen magnum at the base of the skull, or over the ears or inside the ear canal (using an electrode design which fits into the ear canal, such as that shown in PCT application WO 03/059164) also allows current to get into the interior of the skull relatively efficiently.

In some embodiments of the invention, there are more than two such units placed on the head, and, for example, current is passed between different pairs of units while the voltage difference is measured between different pairs of units, not necessarily the same units that current is being passed between. Such an arrangement, using impedance imaging algorithms, can provide additional information about the impedance distribution inside the head, but the data analysis is more complicated than with only two electrodes, and the electrodes take longer to place.

For safety reasons, the units generally use alternating current, for example in the frequency range of a few kilohertz to several tens of kilohertz. Frequencies above about 100 kHz may give impedance data that is less sensitive to blood flow than lower frequencies, since above about 100 kHz the currents can easily flow through the cell membranes, which act like capacitors, and across the interiors of the cells. At frequencies well below 100 kHz, the currents are largely confined to the extra-cellular fluid, and the impedance tends to be more sensitive to blood volume.

Figure 3:
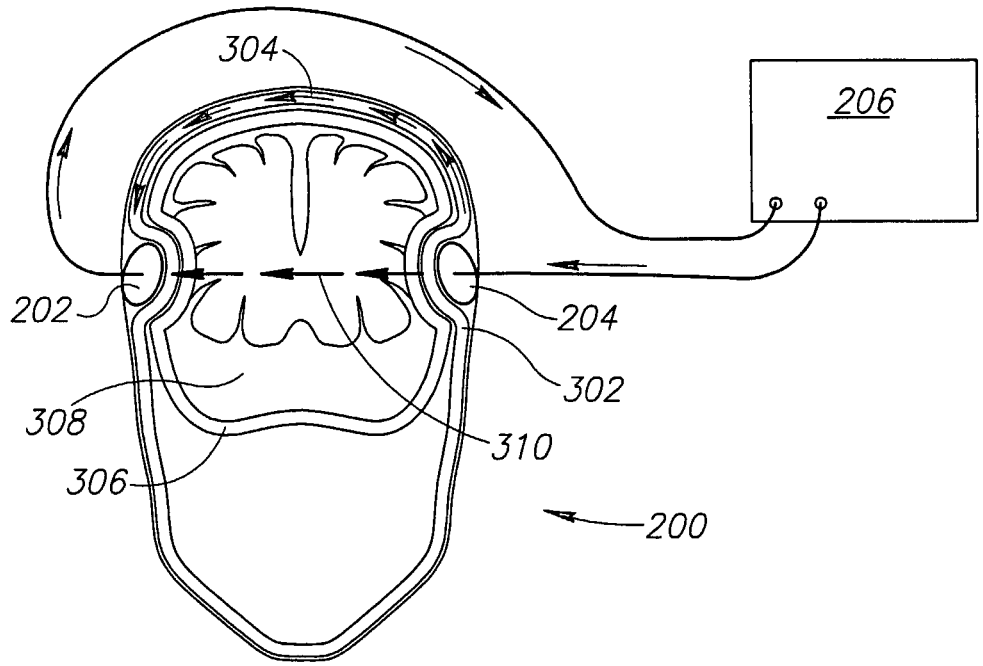
FIG. 3 is a schematic cut-away view of the head with the units placed on it as in FIG. 2, showing current paths through the scalp and through the brain, produced by the IPG electrodes.

FIG. 3 shows a cut-away view of head 200, seen from the front, with units 202 and 204 on the two temples, as in FIG. 2. A cross-sectional cut has been made most of the way through the head in FIG. 3, but in order to show the location of units 202 and 204 on the temples, the skin and skull of the temples have been left in place, in front of the cross-sectional cut. Current between the current electrodes in units 202 and 204 can travel on different paths. Scalp 302 has a relatively low resistivity beneath the epidermis, and a large part of the current travels through the scalp, on path 304, going around skull 306, which has a higher resistivity. Interior 308 of the skull, including the brain and associated blood vessels, also has a relatively low resistivity. Particularly if the current electrodes are fairly wide, a significant part of the current goes through the skull and across the brain, on path 310, since the part of path 310 that goes through the high resistivity skull is relatively short and has wide cross-section, while path 304 through the lower resistivity scalp is much longer and has a much smaller cross-section. If configuration 108 shown in FIG. 1D is used, then a relatively larger part of the current from electrode 110 will tend to go on path 310, through the brain, while a relatively larger part of the current from electrode 114 will tend to go on path 304, through the scalp.

To illustrate how the IPG signal can depend on cerebral blood volume and on scalp blood volume, we note that the impedance R (the ratio of voltage to current) between units 202 and 204 may be expressed as $$R = \frac{R_S R_B}{R_S + R_B}$$

where $R_B$ is the impedance along path 310 through the skull and brain, and $R_S$ is the impedance along path 304 through the scalp, which is parallel to path 310. Each of these impedances has a constant part which is independent of the phase of the cardiac cycle, and a much smaller part which varies with the phase of the cardiac cycle, due to the change in blood volume in the brain and in the scalp. Thus, $$R_B = R_{B0} + \Delta R_B$$

$$R_S = R_{S0} + \Delta R_S$$

Then the impedance between units 202 and 204 may be expressed as $R = R_0 + \Delta R$, where $\Delta R$, the small time varying part of the impedance, is given by $$\Delta R = \frac{R_S}{R_S + R_B} \Delta R_B + \frac{R_B}{R_S + R_B} \Delta R_S$$

to first order in $\Delta R_B$ and $\Delta R_S$. It should be noted that these impedances are mostly resistive at the frequencies typically used, well below 100 kHz, and this is especially true for the variations in the impedances over a cardiac cycle, since they depend on the volume of blood, which is located outside the cell membranes. Higher resistance is associated with a lower volume of blood, so $-\Delta R_B$ and $-\Delta R_S$ are measures respectively of change in cerebral blood volume, and change in blood volume in the scalp. The PPG signal also measures change in blood volume in the scalp, and is approximately a linear function of $-\Delta R_S$ since the signals are small. By subtracting an appropriately weighted PPG signal, proportional to $-\Delta R_S$, from the IPG signal $-\Delta R$, we obtain a signal proportional to $-\Delta R_B$, and hence a linear function of the time-varying part of the cerebral blood volume. One or both of the change in cerebral blood volume over each cardiac cycle and/or the maximum of the time derivative of the cerebral blood volume, are optionally used as an indication of the relative cerebral blood flow.

The cerebral blood volume varies during a cardiac cycle because the arterial blood flow into the brain is pulsatile, while the venous blood flow out of the brain is approximately uniform in time. There is some blood flow into the brain even at the time of diastolic pressure, and this baseline cerebral blood flow cannot be determined directly by measuring changes in cerebral blood volume. However, since the time-varying component is a significant fraction of the total cerebral blood flow, measuring the change in cerebral blood volume during a cardiac cycle may provide a clinically useful relative measure of cerebral blood flow.

Figure 4:
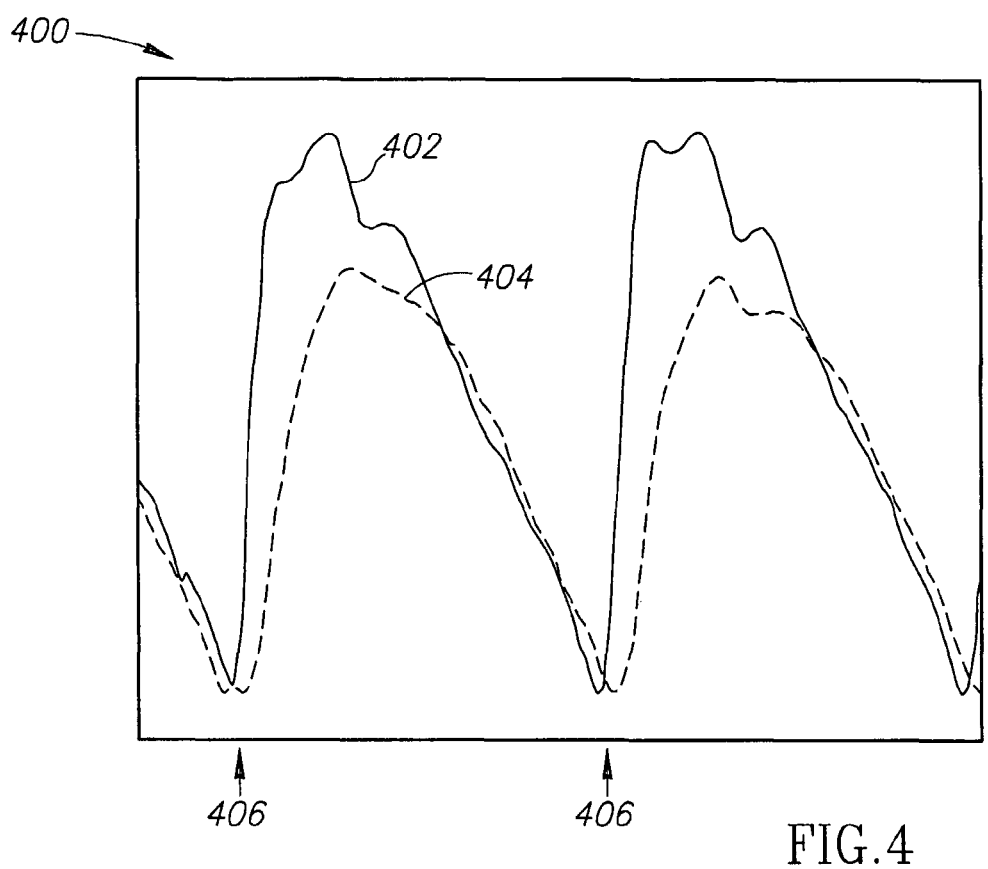
FIG. 4 shows a schematic plot of IPG and PPG signals as a function of time, generated by the units placed on the head as in FIG. 2.

FIG. 4 shows an exemplary plot 400 of the IPG signal $-\Delta R$, labeled 402, shown as a solid curve, and a weighted PPG signal 404, shown as a dashed curve, as a function of time. Signals 402 and 404 are both plotted in arbitrary units, and alternatively signal 404 could be considered the original PPG signal and signal 402 could be weighted, or both signals could be weighted, since only their ratio matters in plot 400. An R-wave, from an electrocardiogram, has peaks at times 406. Note that shortly after the peak of each R-wave, IPG signal 402 and PPG signal 404 both start to rise, as blood flows into the brain and into the scalp, but the rise in the IPG signal starts earlier, and is much more rapid initially, than the rise in the PPG signal. This is believed to be due to the fact that the arteries supplying blood to the brain have a larger diameter, and lower hydrodynamic resistance to blood flow, than the small arteries supplying blood to the scalp. Later in each cardiac cycle, when the blood has had time to flow into the scalp, we expect the IPG signal to be dominated by the blood volume in the scalp. Hence, the weighting factor for PPG signal 404 has optionally been chosen so that weighted PPG signal 404 is approximately equal to IPG signal 402 during an interval late in each cardiac cycle, for example during the last third of each cardiac cycle, when the blood pressure and signals 402 and 404 are falling, before the next peak of the R-wave.

Alternatively, the weighting factor is chosen by other methods which evaluate, at least approximately, the ratio of current through the cranium to current through the scalp.

In some embodiments of the invention, the weighting factor is set equal to the square root of the ratio of the power spectrum of the IPG signal, integrated over a range of frequencies, to the power spectrum of the PPG signal, integrated over the same range. Optionally, the range of frequencies is a range within which the PPG signal is similar to the IPG signal, as indicated, for example, by a high cross-power spectrum between the IPG and PPG signals. For example, the range of frequencies is centered at the peak of the cross-power spectrum, and extends to each side of the peak by an amount equal to or proportional to the rms width of the peak of the cross-power spectrum. Alternatively, the range of frequencies is defined to include all frequencies for which the cross-power spectrum is greater than a certain fraction (for example, half) of the geometric mean of the magnitudes of the IPG and PPG power spectra. Optionally, the two power spectra are weighted within the range of frequencies, for example according to the value of the cross-power spectrum. In this case, the integration over frequency need not be over a limited range of frequencies.

Figure 5:
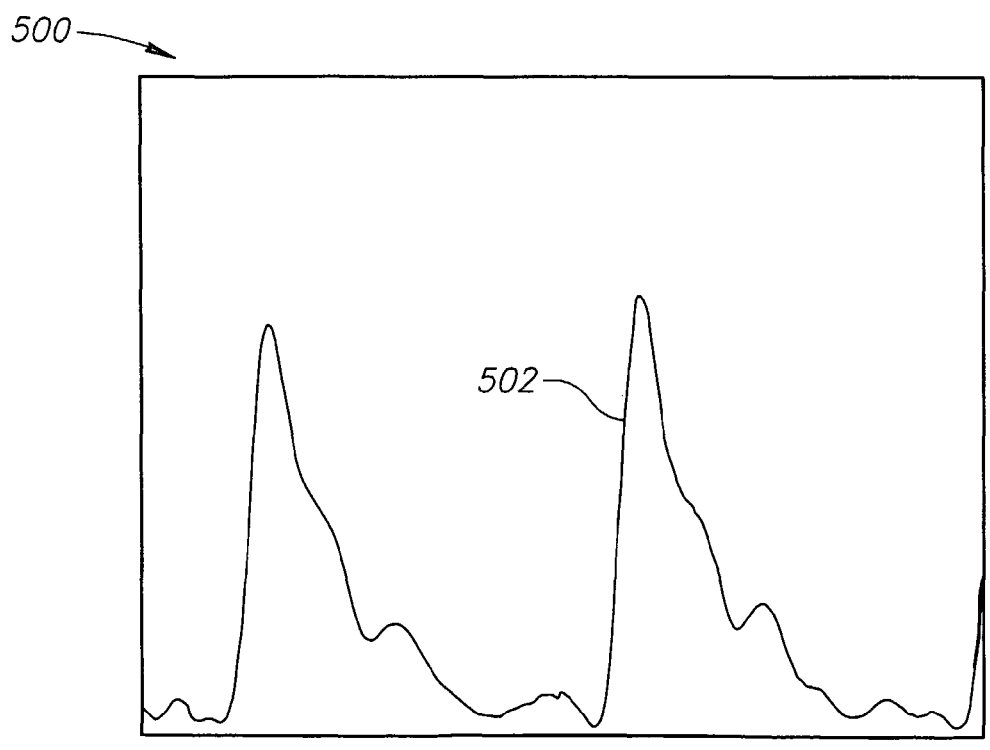
FIG. 5 shows a schematic plot of the variation in cerebral blood volume as a function of time during two cardiac cycles, derived by taking a difference between the IPG signal and the PPG signal shown in FIG. 4.

FIG. 5 shows a plot 500 of a signal 502 equal to the difference between IPG signal 402 and weighted PPG signal 404, as a function of time.

Figure 6:
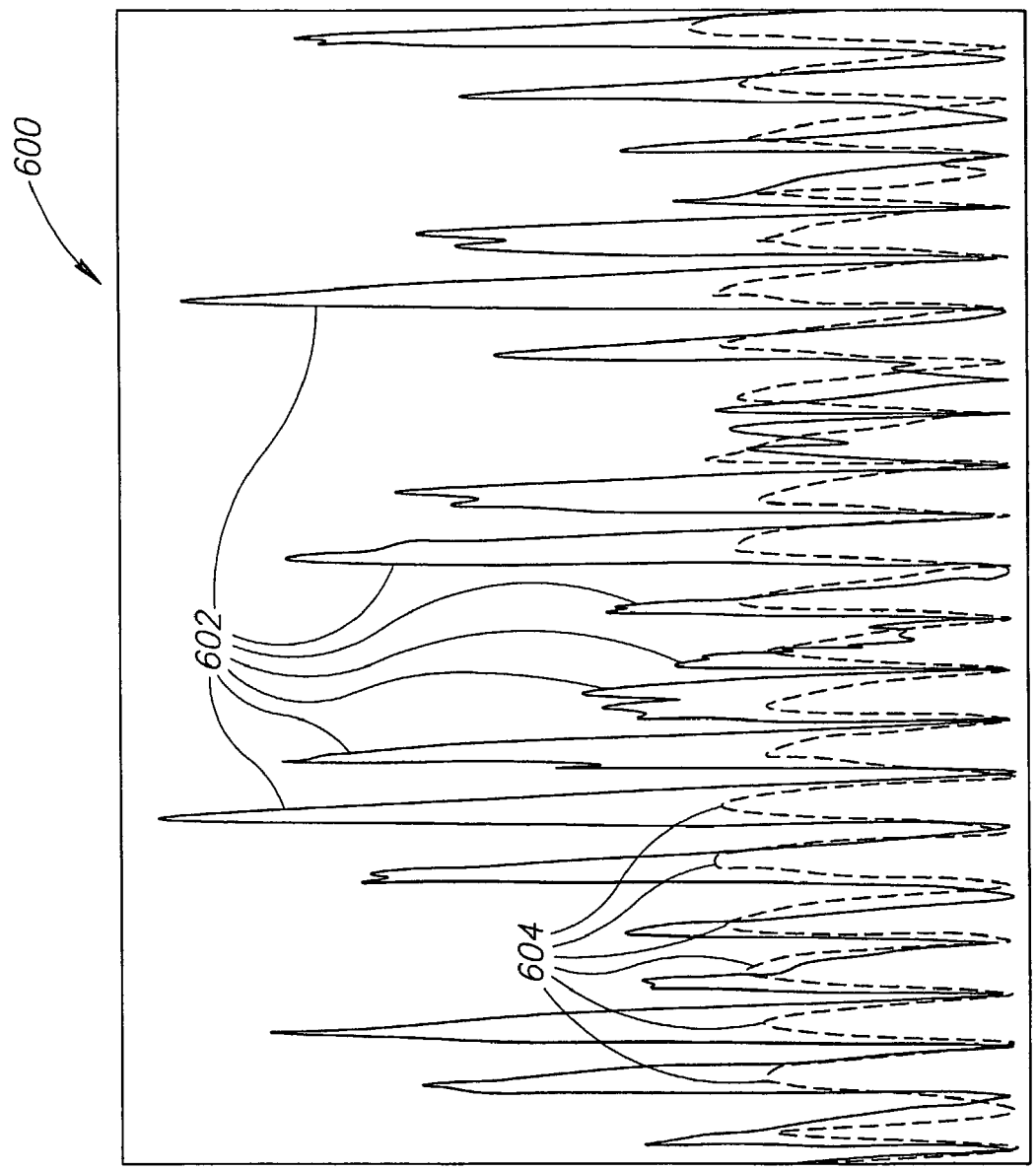
FIG. 6 shows a schematic plot of IPG and PPG signals as a function of time, similar to the signals shown in FIG. 4, but extending over a longer time interval and measured while the subject is hyperventilating.

In some embodiments of the invention, the cerebral blood volume is estimated from the IPG signal alone. This may be justified because there is evidence that early in each cardiac cycle, and even up to the peak in the IPG signal, the time-dependent part of the IPG signal is largely dominated by changes in cerebral blood volume. For example, FIG. 6 shows a plot 600 of an IPG signal 602, plotted as a solid line, and a PPG signal 604, plotted as a dashed line, measured while the subject was voluntarily hyperventilating. The hyperventilation produces large fluctuations in the peak value of the IPG signal from one cardiac cycle to another, and much smaller fluctuations in the peak value of the PPG signal from one cardiac cycle to another. Since the time dependence of the PPG signal is believed to be due almost entirely to changes in the scalp blood volume, the fact that the IPG signal behaves very differently from the PPG signal indicates that the IPG signal is not dominated by the changes in scalp blood volume, but by something else, presumably changes in cerebral blood volume. One method of estimating the time varying part of the cerebral blood volume is just to assume that the change in cerebral blood volume is proportional to the peak value of the IPG signal for each cardiac cycle.

Figure 7:
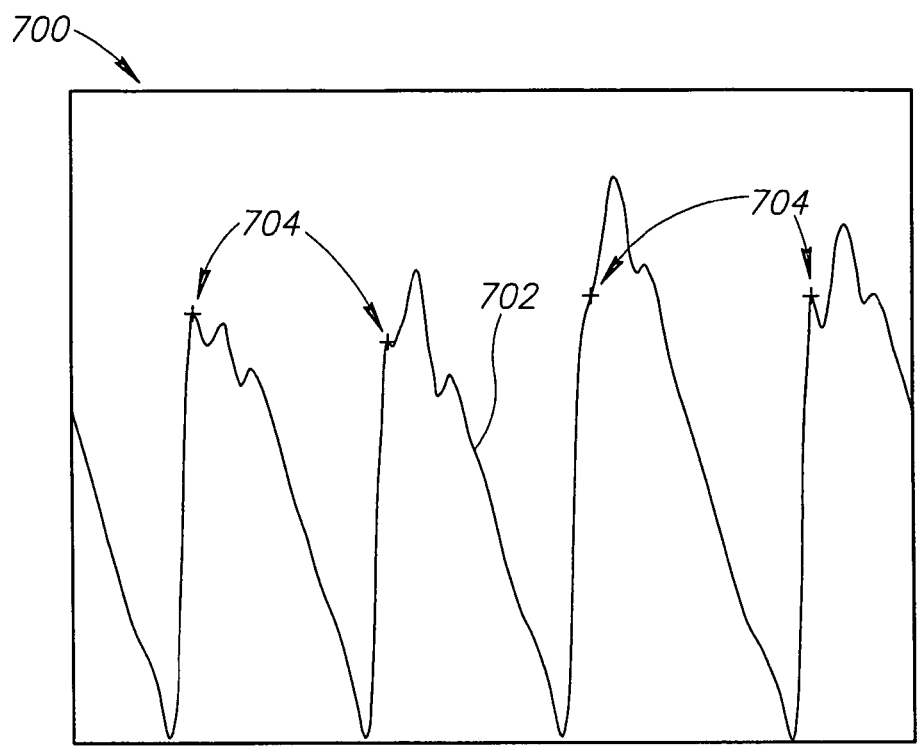
FIG. 7 shows a schematic plot of an IPG signal as a function of time, illustrating a method of estimating changes in cerebral blood flow according to an exemplary embodiment of the invention.

FIG. 7 illustrates another method of estimating the changes in cerebral blood volume, again using only the IPG signal. Plot 700 shows an IPG signal 702 as a function of time, for four cardiac cycles. In each cardiac cycle, the value of the IPG signal is measured at its first local peak following the minimum (or following the peak in the R-wave, which occurs at about the same time as the minimum in the IPG signal). Optionally, if there is an inflection point in the IPG signal before the first local peak, then the value of the IPG signal is measured at the inflection point. This is true, for example, in the third cardiac cycle shown in plot 700. These values of the IPG signal for each cardiac cycle are indicated by small crosses 704 in plot 700. Using these values of the IPG signal in each cardiac cycle may better reflect the change in cerebral blood volume than using the peak IPG signal in each cardiac cycle. This may be true, for example, because these values occur earlier in each cardiac cycle, when the IPG signal is more dominated by the time-dependent part of the cerebral blood volume, and is less sensitive to the scalp blood volume.

Figure 8:
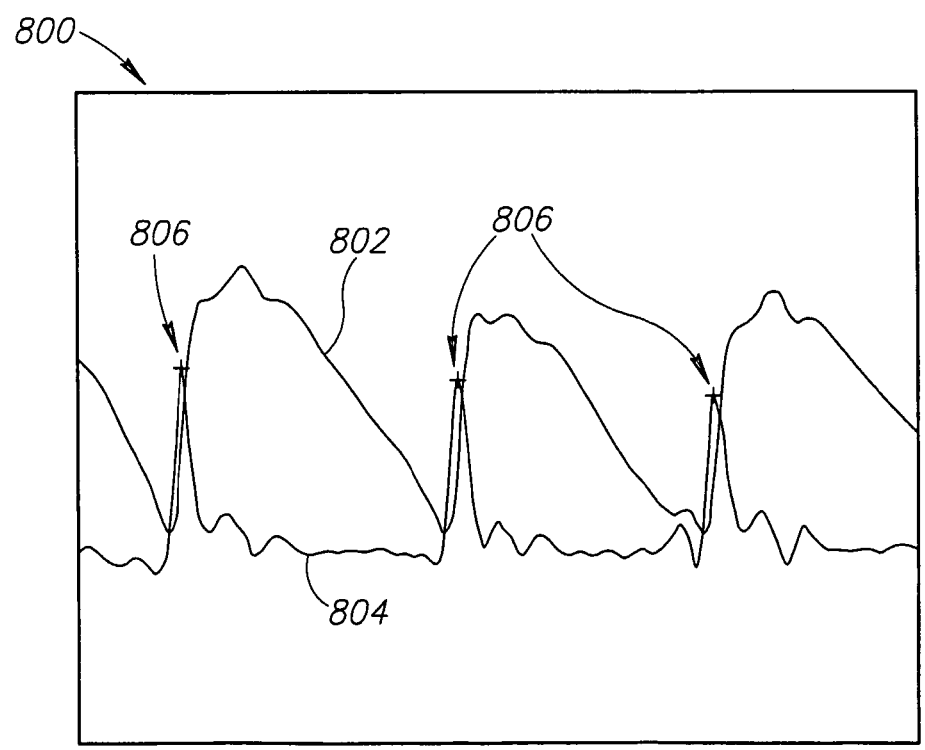

FIG. 8 illustrates yet another method of estimating the changes in cerebral blood volume, using only the IPG signal. Plot 800 shows an IPG signal 802 as a function of time, for three cardiac cycles, and a signal 804 proportional to the time derivative of IPG signal 802. The peak of signal 804, i.e. the peak rate of rise of IPG signal 802, is measured in each cardiac cycle, and indicated by small crosses 806 in plot 800. To the extent that the peak in signal 804 occurs early enough in each cardiac cycle that IPG signal 802 is still dominated largely by changes in cerebral blood volume rather than by changes in scalp volume, the peak value of signal 804 may be a good indication of the change in cerebral blood volume during that cardiac cycle, perhaps a better indication than the peak value of the IPG signal.

In any of the methods illustrated in FIGS. 6-8, the PPG signal is optionally recorded as well, for example to verify that the scalp blood volume is not changing very much early in each cardiac cycle, at the times when the IPG signal is used to estimate the change in cerebral blood volume. In some embodiments of the invention, two or more of the methods illustrated in FIGS. 5-8 are used to estimate the change in cerebral blood volume, for example by taking a weighted average of the change in cerebral blood volume determined by each method. Different methods might work best for different patients who have different medical conditions. For example, if a patient is suffering from a condition in which cerebral blood flow is likely to be reduced more than scalp blood flow, then the changes in scalp blood flow may dominate the IPG signal even early in the cardiac cycle, and it may be best to use the method illustrated in FIG. 5, which makes use of both the IPG signal and the PPG signal. In a case where cerebral blood flow and scalp blood flow are likely to be reduced at the same time, for example in the case of a patient undergoing cardiac surgery, it may be better or easier to use one of the methods that depends only on the IPG signal.

The invention has been described in the context of the best mode for carrying it out. It should be understood that not all features shown in the drawings or described in the associated text may be present in an actual device, in accordance with some embodiments of the invention. Furthermore, variations on the method and apparatus shown are included within the scope of the invention, which is limited only by the claims. In addition, while the invention has been described in some cases mainly as method, the scope of the invention also includes apparatus programmed to perform the method, for example, dedicated circuitry, hardware, firmware and/or software, including computer-readable media with suitable software thereon. Also, features of one embodiment may be provided in conjunction with features of a different embodiment of the invention. As used herein, the terms "have", "include" and "comprise" or their conjugates mean "including but not limited to."

The invention claimed is:

1. A method of estimating cerebral blood flow, comprising:
   a) obtaining a measure of time-varying blood volume in the head, using impedance plethysmography electrode units that pass current through the head;
   b) obtaining a measure of time-varying blood volume in the scalp using a plethysmography sensor; and
   c) weighting the measures of time-varying blood volume in the head and time-varying blood volume in the scalp
   d) estimating the cerebral blood flow from the weighted measures of time-varying blood volume in the head and time-varying blood volume in the scalp.

2. A method according to claim 1, wherein obtaining a measure of time-varying blood volume in the scalp comprises using photoplethysmography.

3. A method according to claim 1, wherein estimating the cerebral blood flow comprises estimating the relative cerebral blood flow as it changes over time.

4. A method according to claim 1, wherein the measures of time-varying blood volume are weighted to have at least approximately the same value at a time in the cardiac cycle when the blood pressure is falling.

5. A method according to claim 1, wherein the measures of time-varying blood volume are weighted to have approximately equal power spectra at frequencies for which the cross-power spectrum between the measures of time-varying blood volume is relatively high.

6. A method according to claim 1, wherein obtaining a measure of blood volume in the head using impedance plethysmography comprises:
   a) passing a current through the head using two current-carrying electrodes; and
   b) measuring a voltage across the head, associated with the current, using two voltage-measuring electrodes.

7. A method according to claim 6, also including applying to the head an annular electrode surrounding at least one of the current-carrying electrodes, and maintaining the annular electrode at a same voltage as the current-carrying electrode it surrounds, thereby suppressing radial current from said current-carrying electrode.

8. A method according to claim 6, wherein the voltage-measuring electrodes are distinct from, and substantially electrically decoupled from, the current-carrying electrodes.

9. A method according to claim 6, wherein obtaining a measure of blood volume in the head using impedance plethysmography comprises placing the two current-carrying electrodes on the left and right temples respectively.

10. A method according to claim 6, wherein obtaining a measure of blood volume in the head using impedance plethysmography comprises placing each of the two voltage-measuring electrodes on the head in a position adjacent to a different one of the current-carrying electrodes.

11. A method according to claim 10, wherein obtaining a measure of blood volume in the scalp using photoplethysmography comprises placing a photoplethysmography sensor on the head adjacent to one of the current-carrying electrodes and to the voltage-measuring electrode which is adjacent to said current-carrying electrode.

12. A unit for estimating cerebral blood flow, adapted for placing on the head, the unit comprising:
   a) at least one electrode unit adapted to pass current through the head for impedance plethysmography, and adapted to be placed on the head so that a significant part of the current goes through the brain, the electrode unit comprising:
      i) a current-carrying electrode adapted for injecting current through the head when it is placed on the skin; and
      ii) a voltage-measuring electrode adapted for measuring voltage across the head when it is placed on the skin, and when the current-carrying electrode is injecting current; and
   b) a plethysmography sensor adapted for measuring blood flow in a scalp; adapted for use in infant patients, wherein the current-carrying electrode comprises an annulus surrounding the voltage-measuring electrode, and the radial thickness of the annulus and the gap between the current-carrying and voltage-measuring electrodes are each at least twice as great as a typical thickness of the epidermis in said infant patients.

13. A unit according to claim 12, wherein the radial thickness of the annulus and the gap between the current-carrying and voltage-measuring electrodes are each at least 1 mm.

14. A unit according to claim 13, wherein the radial thickness of the annulus and the gap between the current-carrying and voltage-measuring electrodes are each at least 2 m.

15. A system for estimating cerebral blood flow, comprising:
   a) at least one plethysmography sensor adapted for measuring time-varying blood volume in a scalp;
   b) an impedance measuring unit comprising at least two electrode units adapted for placing on the head and performing impedance plethysmography to measure time-varying blood volume in the head;
   c) a power supply adapted for passing current across the head between the at least two electrode units of the impedance measuring unit, when said electrode units are placed on different sides of the head; and
   d) a data analyzer which calculates a cerebral blood flow using a weighted difference between impedance data on time-varying blood volume of the head obtained from the impedance measuring unit, and data on time-varying blood volume in the scalp generated by the plethysmography sensor.

16. A system according to claim 15, wherein the plethysmography sensor and at least one of the electrode units of the impedance measuring unit are combined in a single structure.

* * * * *